United States Patent [19]

Gonzalez, Jr.

[11] 4,139,004

[45] Feb. 13, 1979

[54] BANDAGE APPARATUS FOR TREATING BURNS

[76] Inventor: Harry Gonzalez, Jr., 342 3rd Ave., La Puente, Calif. 91744

[21] Appl. No.: 769,443

[22] Filed: Feb. 17, 1977

[51] Int. Cl.² .............................................. A61N 1/00
[52] U.S. Cl. .................................. 128/82.1; 128/400; 128/402
[58] Field of Search ..................... 128/82.1, 399, 400, 128/402, 155, 156, 157, DIG. 4

[56] References Cited

U.S. PATENT DOCUMENTS

| | | | |
|---|---|---|---|
| 26,663 | 1/1860 | French | 128/402 X |
| 2,577,945 | 12/1951 | Atherton | 128/156 |
| 2,584,302 | 2/1952 | Stein | 128/399 X |
| 2,749,914 | 6/1956 | Braley | 128/402 |
| 2,943,627 | 7/1960 | Howell | 128/DIG. 4 |
| 3,149,943 | 9/1964 | Amador | 128/402 X |
| 3,612,059 | 10/1971 | Ersek | 128/399 |
| 3,867,939 | 2/1975 | Moore et al. | 128/254 |
| 3,901,225 | 8/1975 | Sconce | 128/402 X |

*Primary Examiner*—John D. Yasko
*Attorney, Agent, or Firm*—Boniard I. Brown

[57] ABSTRACT

A bandage apparatus for the treatment of burns, said bandage having various sizes and shapes for direct contact with any particular area of the human body so affected, the bandage being provided to promote rapid healing, and to reduce pain and the possibility of infection associated therewith, wherein a metallic member is brought into direct contact with the burned portion. The bandage comprises a metallic member formed from any suitable material—such as metal foil or various metal fabrics—being enclosed as an inner liner of an envelope having a pair of plastic sheets defining a sealable chamber adapted to receive various fluid coolants therein such as air, gas or liquid, the envelope being provided with a protective cover.

16 Claims, 12 Drawing Figures

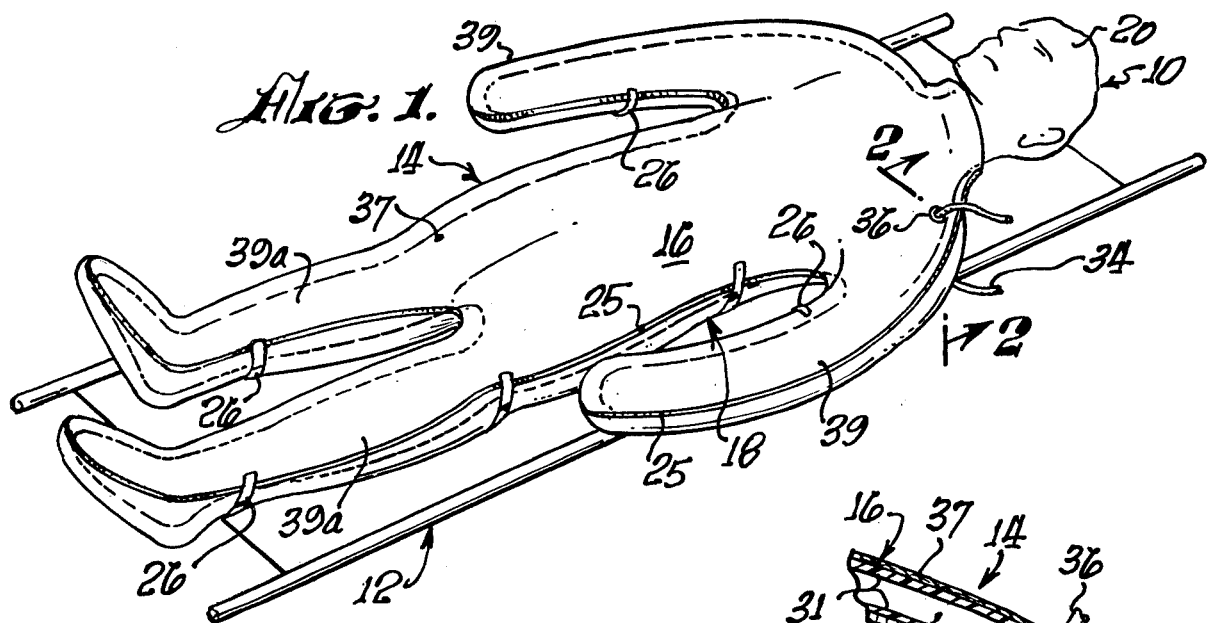
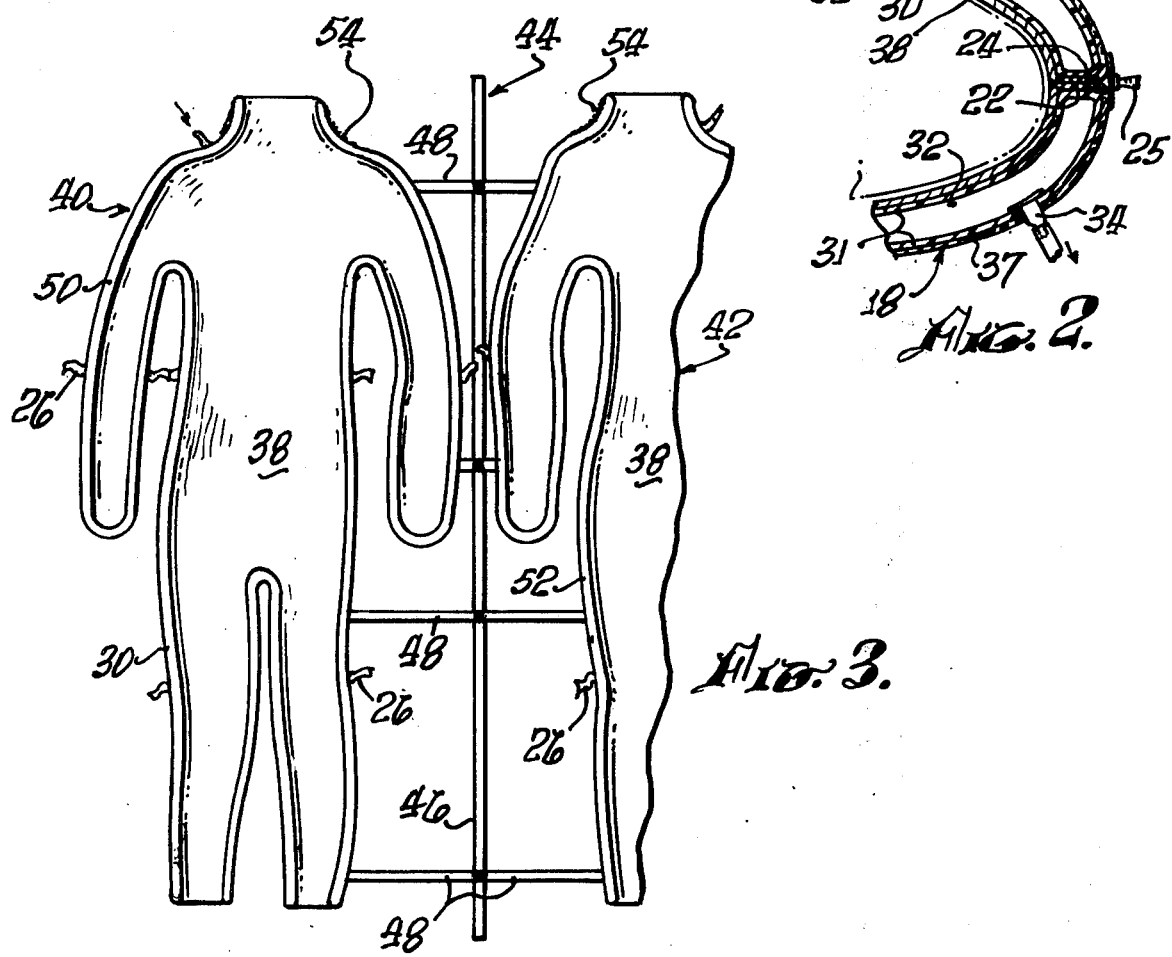

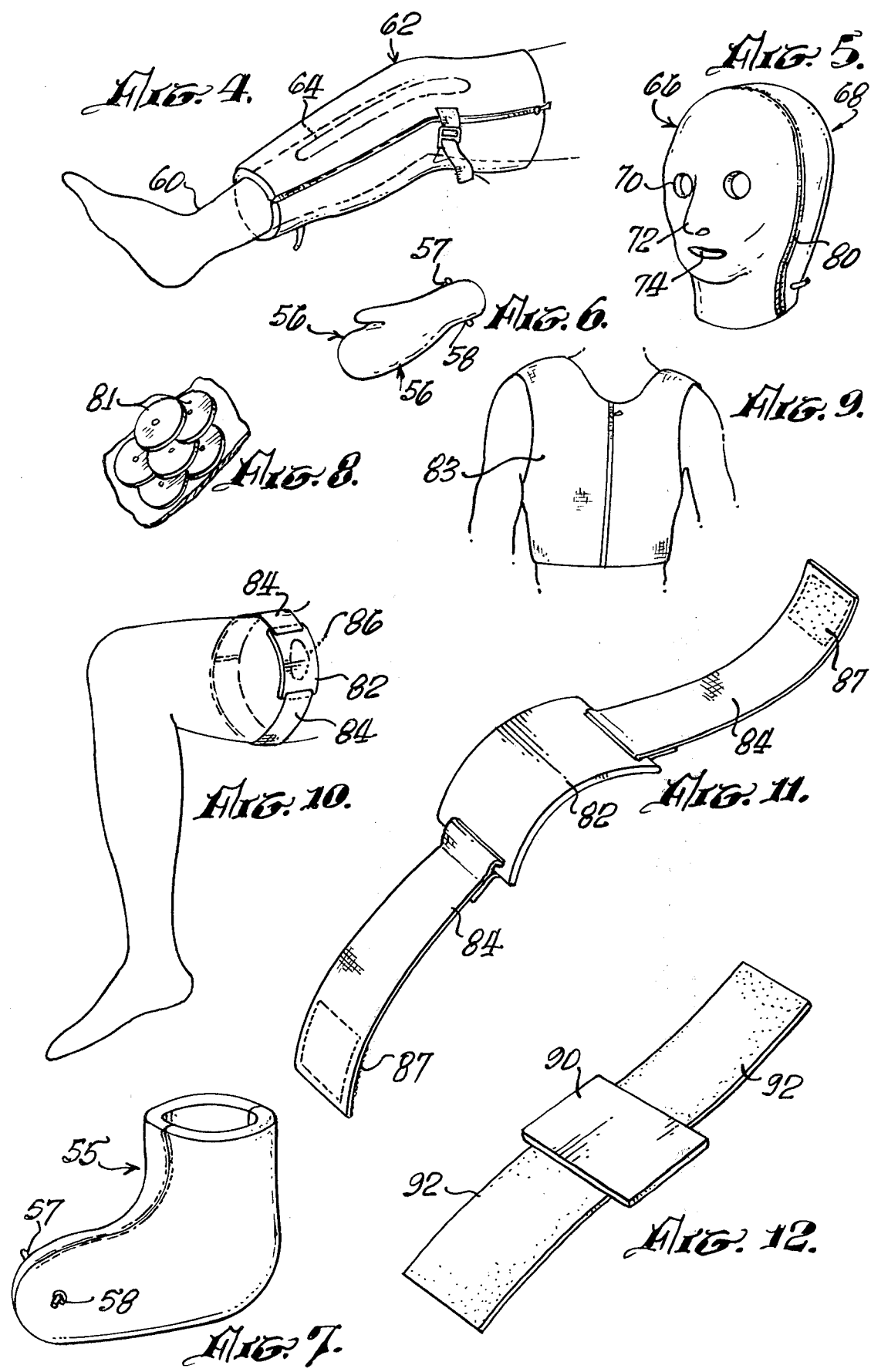

BANDAGE APPARATUS FOR TREATING BURNS

BACKGROUND OF THE INVENTION

1. Field of the Invention

This invention relates to bandages and, more particularly, to bandages that are applied to burns, wherein various sizes and shapes of bandages include a metallic sheet for direct contact to the affected burned area, whether it be a particular portion of the body or the entire body.

2. Description of the Prior Art

As is well known in the art, various problems and difficulties are encountered in providing suitable means for treating the burn areas of the human body.

Several methods of treating burns are now available and are in use today. However, it is felt that there are areas of treatment that are lacking and need to be resolved. There is a constant search in the medical field to provide a bandage that is more suitable to burns, wherein the bandage is constructed not only to protect the affected, traumatized areas, but can also act as a means to accelerate healing, thus producing a superior healing method and, if possible, relieving pain or reducing it to a minimum.

Recently, it has been found that cooling or coolants applied to burn areas not only make the patient more comfortable by reducing pain, but promote the healing process as well by reducing inflammatory edema and infection, and minimizing tissue damage.

Thus, with the use of the present apparatus as disclosed, the treatment of burns can be greatly improved upon.

SUMMARY OF THE INVENTION

The present invention has been developed to treat burned areas of flesh on the human body, wherein a metal object that is preferably cooler than body temperature is placed against the burned area of flesh as soon as possible after the burn is sustained, ideally immediately thereafter or at least within minutes after the occurrence thereof. It has been noted that the cooler the metal object, the better the result. However, a repeated contact or a relatively continuous contact of the metallic member is more important than coolness of the metal itself.

Thus, the present device can be formed as a simple "Bandaid"-type or a sophisticated unit having a coolant adapted to be employed thereiwth, as will be hereinafter disclosed.

The "Bandaid"-type comprises a flexible sheet of metal having fastening devices such as the known adhesive tapes and like fasteners so as to be readily applied to small, localized burn areas.

With respect to large affected areas, the device comprises various shapes and sizes of a sealable envelope having an inner sheet formed from any metallic material, such as thin foil, or various metallic fabrics, and including an outside protective cover of a canvass-like material. The envelope is arranged to have a chamber defined by a pair of plastic sheets adapted to receive therein a coolant of fluid such as air, water, or gas by means of control valves. Thus, the metallic inner liner can be kept at any desired temperature, particularly a temperature cooler than the affected burn area.

It is contemplated that such a device can be formed to cover the entire body or portions thereof.

OBJECTS AND ADVANTAGES OF THE INVENTION

The present invention has for an important object a provision wherein burn areas of a body are treated by placing a metallic object or member, preferably cool, directly in contact with the affected area.

It is another object of the invention to provide a bandage specifically designed to be applied to the burn area of an individual, said bandage having an envelope to receive a coolant therein; and wherein the inner liner of the envelope comprises a metal foil, or a metallic cloth or fabric, having the temperature thereof controlled by the coolant within the envelope.

It is further another object of the present invention to provide a bandage apparatus that will cover the entire body structure so that a relatively continuous contact between the body and metallic liner is created.

A further object of the invention is to provide a bandage for burns that will help to reduce pain, accelerate healing, and prevent infection.

It is a further object of the invention to provide an apparatus of this character wherein the coolant employed therewith can be air, water, or gas.

A still further object of the invention is to provide a bandage of this type that is easily applied to any size body; and wherein various units are designed for legs, arms, feet, hands, head, etc.

It is another object of the invention to provide a bandage of this character that allows healing to occur if the burn has already blistered; and the burn will scab without pain or infection.

It is still another object of the invention to provide an apparatus of this character that is easy to service and maintain.

The characteristics and advantages of the invention are further sufficiently referred to in connection with the accompanying drawings, which represent one or more embodiments. After considering these examples, skilled persons will understand that variations may be made without departing from the principles disclosed and I contemplate the employment of any structures, arrangements or modes of operation that are properly within the scope of the appended claims.

BRIEF DESCRIPTION OF THE DRAWINGS

Referring more particularly to the drawings, which are for illustrative purposes only:

FIG. 1 is a pictorial view of the present invention, showing the type that fully covers the patient's body;

FIG. 2 is an enlarged cross-sectional view taken substantially along line 2—2 of FIG. 1 wherein the structure of the envelope is shown including an inlet and outlet means, to allow continuous flow of coolant therethrough;

FIG. 3 is a plan view of the body bandage wherein each half of the body bandage is separated and includes hinging means to connect each section in a restrained position;

FIG. 4 is a perspective view of an alternative arrangement wherein the unit is designed to be positioned on a leg having a burn area;

FIG. 5 is a perspective view of the present invention formed as a face bandage;

FIG. 6 is a perspective view of a further unit of the invention forming a bandage cover for burns located on the hands;

FIG. 7 is a perspective view of the invention formed as a foot boot to cover the related body area thereof;

FIG. 8 is a pictorial view of a metal liner being formed from a plurality of metal plates;

FIG. 9 is a plan view of the invention formed as a jacket having a metal liner formed by chain links;

FIG. 10 is a pictorial view, illustrating the device as a strip bandage applied to the upper portion of a leg having a burn area of small size;

FIG. 11 is a perspective view of the unit having a metal member and extending straps, including fastening means thereon; and FIG. 12 is another arrangement having a metal member wherein the extending straps are formed from adhesive strips.

DESCRIPTION OF THE PREFERRED EMBODIMENT

Referring more particularly to FIGS. 1 through 3, there is shown a burn victim, generally indicated at 10, who represents a burn patient supported in a well-known, conventional stretcher 12, wherein the individual has his or her entire body encapsulated within the bandage apparatus shown as an inflated envelope, generally designated at 14. Said envelope comprises a front first half section 16 which is formed in a manner to readily conform to the general configuration of the front surface area of the victim, and a rear second half section 18 which is formed in a manner to readily receive the rear contour of the body. Thus, it can be seen that the design configuration of the encapsulating bandage covers most of the patient's body, with the exception of the head 20.

Before a more detailed description of the bandage is provided, it should be noted that both the hands and the feet can also be exposed if needed, and thereby be provided with separately designed bandages as will hereinafter be described.

Accordingly, FIG. 1 illustrates total encapsulation of the body with the exception of the head 20, wherein front section 16 is removably attached to the rear section 18 by fastening means that allows for ease of coupling the two halves together, and includes the sealing of each half along its peripheral contacting edges 22 and 24, respectively. The most suitable fastening means has been found to be a continuous zipper 25 attached to each half section in the well-known manner.

As added security, the two half sections 16 and 18 are provided with belt latches 26 located along the zipper connection, to prevent separation if the patient becomes very restless.

The construction of each half section is identical and comprises envelope 30 formed by a sheet or a pair of sheets 31 of an impervious material such as plastic or the like, providing leak-proof liners which, when formed as an envelope, define a sealed chamber 32, as illustrated in FIG. 2. Thus, the chamber is arranged to receive various fluids therein, such as air, gas, water or any other types of liquids that are used as coolants. Accordingly, each chamber includes an outlet 34 and inlet 36, whereby any of the above fluids can be circulated through chamber 32. To protect the outer surface of the envelope, it is covered by a canvas or cloth cover sheet 37, defining an outer liner.

Moreover, there is provided an inner metallic liner means 38 which is arranged to come into direct contact with the patient's body, particularly the burned area that is to be treated, said inner liner 38 being formed of a metallic substance so as to provide a cool surface to the affected burn areas. Various types of metallic material are contemplated, such as metal foil, metal screening, metal woven fabrics or small interconnected chain links. In the embodiment of FIG. 1, the bandage is arranged having a pair of arm portions 39 and leg members 39a. The arm portions are designed to cover the hands as well, and the leg members include boot portions to cover the victim's feet.

It is important to the treatment of burns that the burn area be kept cool; and, thus, by providing a continuous metallic liner as that of 38, healing can be accelerated and pain reduced to a minimum.

Thus, as the coolant fluid is passed through the adjacent chambers, the cooling reaction is transferred to the metallic liner 38, and then to the patient's flesh.

Referring to FIG. 3, there is shown another embodiment wherein the two sections 40 and 42 are first hinged together by hinging means 44. This hinge means can be formed in any suitable manner and is shown herein as having a central hinge bar 46 with laterally extending, hinge arms 48, said arms being secured to each half section so that sections 40 and 42 can be folded over, allowing respective peripheral edges 50 and 52 thereof to contact each other in sealing engagement, whereby the zippers 54 are connected. In the embodiment of FIG. 3, it should be noted that hand and foot receiving member portions are not provided. Thus, when necessary, a boot-shaped bandage, generally indicated at 55 in FIG. 7, can be provided. This is also true with respect to the bandage area that covers the hands as shown in the first embodiment. That is, a glove or mitten, designated at 56 in FIG. 6, can be employed. Hence, boot 55 and mitten 56 are both provided with their individual inlets and outlets to allow coolant fluids to be received therein in a similar manner as hereinbefore described, the respective inlet and outlet members being indicated at 57 and 58, respectively.

When a patient's hand or foot is affected and needs treatment, then only the mitten or boot is required, depending upon the particular burn area.

It is further comtemplated that several bandage designs may be included, one being that as shown in FIG. 4 wherein the bandage comprises an envelope capable of being wrapped around a leg 60, as illustrated, or an arm. The configuration and arrangement of bandage 62 can be readily adapted for use with any portion of the extremities that might be affected by a burn, such as indicated at 64 on leg 60.

For facial burns, an arrangement as shown in FIG. 5 is contemplated wherein first and second half sections 66 and 68 are provided, section 66 being designed to accommodate the eye, nose and mouth of a patient wherein respective openings 70, 72, and 74 are included therein. The rear section 68 is fastened to the front section 66 by zipper 80. The detailed structure of each individual bandage unit, boot, mitten, head mask, etc., is constructed as described for the preferred embodiment having an inner metallic liner of any suitable material, to conform to the body configuration and a coolant chamber.

An additional inner liner is also contemplated whereby the liner comprises a plurality of metal-plate sequins 81 arranged to overlap each other, similar to that of a dress fabric having sequins attached thereto, as shown in the enlarged fragmentary view of FIG. 8.

The form of the invention shown in FIG. 9 is a vest-like or jacket-type covering 83 formed of overlapping sequins, such as are illustrated in FIG. 8, or formed of mail-like woven metallic cloth.

A simple form of the present invention is shown in FIGS. 10 through 12, wherein there is shown a metal plate or strip 82 having fastening straps 84 attached to opposite ends thereof in a suitable manner. In FIG. 10, the bandage is illustrated attached to the upper portion of the leg, wherein plate 82 contacts a burn area 86. The straps 84 are provided with suitable securing means, said means being shown in FIG. 11 as fabric-securing pads 87 known under the trademark of "Velco".

In FIG. 12, an even more simple form is shown having a metal plate 90, including adhesive straps 92 which are well known in the art.

The invention and its attendant advantages will be understood from the foregoing description; and it will be apparent that various changes may be made in the form, construction and arrangement of the parts of the invention without departing from the spirit and scope thereof or sacrificing its material advantages, the arrangements hereinbefore described being merely by way of example; and I do not wish to be restricted to the specific forms shown or uses mentioned, except as defined in the accompanying claims.

The inventor claims:

1. A bandage having a coolant transfer means adapted for use in accelerating healing and reducing pain relating to burn areas of the human body, wherein the bandage comprises:
   an envelope having sealed inner and outer sheets of impervious material and defining a chamber;
   an outer protective cover attached to said outer impervious sheet;
   an inner pliable metallic liner secured to said inner impervious sheet arranged to directly contact said burn area;
   an inlet means mounted in said envelope;
   an outlet means mounted in said envelope;
   coolant means to be circulated through said chamber wherein the temperature of said coolant is transferred to said metallic liner; and
   fastening means to secure the bandage to the body.

2. A bandage as recited in claim 1, wherein said bandage comprises:
   a first front half section wherein the envelope thereof is formed to receive the front surface of said body; and
   a second rear half section wherein the envelope thereof is formed to receive the rear surface of said body, each of said half sections having contacting, peripheral edges held in sealing engagement by said fastening means thereof.

3. A bandage as recited in claim 2, wherein said front and rear half sections are arranged to encapsulate the entire body of a burn victim to a point below the head thereof.

4. A bandage as recited in claim 3, wherein said front and rear half sections include:
   a pair of leg portions;
   a pair of arm portions; and
   a main body portion wherein said portions are integrally formed.

5. A bandage as recited in claim 4, wherein:
   said leg portions terminate adjacent the ankle of said body; and
   said arm portions terminate at the wrist of said body.

6. A bandage as recited in claim 4, wherein said bandage includes hinge means secured to each oppositely disposed half sections.

7. A bandage having a coolant transfer means adapted for use in accelerating healing and reducing pain relating to burn areas of the human body, wherein the bandage comprises:
   an envelope having sealed inner and outer sheets of impervious material and defining a chamber;
   an outer protective cover attached to said outer impervious sheet;
   an inner pliable metallic liner secured to said inner impervious sheet arranged to directly contact said burn area;
   an inlet means mounted in said envelope;
   an outlet means mounted in said envelope;
   coolant means to be circulated through said chamber wherein the temperature of said coolant is transferred to said metallic liner;
   the bandage having a first front half section wherein the envelope thereof is formed to receive the front surface of said body and a second rear half section wherein the envelope thereof is formed to receive the rear surface of said body, said sections being arranged to encapsulate the entire body below the head and include integrally formed legs, arms and body portions;
   a central hinge bar;
   laterally extending arm members hinged to said hinge bar and secured to the respective half sections; and
   fastening means to secure the bandage to the body by holding peripheral edges of the first and second half sections in sealing engagement.

8. A bandage as recited in claim 1, wherein said inner metallic liner comprises a sheet of metal foil.

9. A bandage as recited in claim 1, wherein said inner metallic liner comprises a metal woven fabric.

10. A bandage having a coolant transfer means adapted for use in accelerating healing and reducing pain relating to burn areas of the human body, wherein the bandage comprises:
    an envelope having sealed inner and outer sheets of impervious material and defining a chamber;
    an outer protective cover attached to said outer impervious sheet;
    an inner pliable metallic liner comprising a plurality of metal plates attached to cloth material and secured to said inner impervious sheet arranged to directly contact said burn area;
    an inlet means mounted in said envelope;
    an outlet means mounted in said envelope;
    coolant means to be circulated through said chamber wherein the temperature of said coolant is transferred to said metallic liner;
    the bandage having a first front half section wherein the envelope thereof is formed to receive the front surface of said body and a second rear half section wherein the envelope thereof is formed to receive the rear surface of said body, said sections being arranged to encapsulate the entire body below the head and include integrally formed legs, arms and body portions;
    fastening means comprising a zipper attached along the adjacent contacting edges of said envelope with belt latches sequentially located along the zipper to secure the bandage to the body.

11. A bandage as recited in claim 2, wherein said front and rear sections form a head bandage wherein said front section includes eye, nose and mouth openings therein.

12. A bandage as recited in claim 1, wherein said envelope comprises a boot configuration to cover the foot of a body.

13. A bandage as recited in claim 1, wherein said envelope comprises a mitten to cover the hand of a body.

14. A bandage as recited in claim 1, wherein the envelope is configurated and sized to fit about a leg of the human body.

15. A bandage as recited in claim 1, wherein the envelope is configurated and sized to fit about an arm of the human body.

16. A bandage as recited in claim 1, wherein the inner metallic liner comprises a plurality of metal plates secured to a cloth backing material.

* * * * *